: US 9,254,392 B2
: Feb. 9, 2016

(12) United States Patent
Ghosh et al.

(54) ANODAL CAPTURE DETECTION

(71) Applicant: Medtronic, Inc., Minneapolis, MN (US)

(72) Inventors: Subham Ghosh, Minneapolis, MN (US); Todd Sheldon, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 206 days.

(21) Appl. No.: 14/145,053

(22) Filed: Dec. 31, 2013

(65) Prior Publication Data

US 2015/0182751 A1 Jul. 2, 2015

(51) Int. Cl.
*A61N 1/37* (2006.01)
*A61N 1/362* (2006.01)

(52) U.S. Cl.
CPC .............. *A61N 1/371* (2013.01); *A61N 1/362* (2013.01)

(58) Field of Classification Search
CPC .... A61N 1/371; A61N 1/3684; A61N 1/3712
USPC .......................................................... 607/28
See application file for complete search history.

(56) References Cited

U.S. PATENT DOCUMENTS

| 4,428,378 A | 1/1984 | Anderson et al. |
|---|---|---|
| 5,052,388 A | 10/1991 | Sivula et al. |
| 6,393,316 B1 | 5/2002 | Gillberg et al. |
| 7,684,863 B2 | 3/2010 | Parikh et al. |
| 7,917,214 B1 | 3/2011 | Gill et al. |
| 2008/0177344 A1 | 7/2008 | Maskara et al. |
| 2008/0306567 A1 | 12/2008 | Park et al. |
| 2010/0121396 A1 | 5/2010 | Gill et al. |
| 2010/0121404 A1 | 5/2010 | Björling et al. |
| 2010/0262204 A1 | 10/2010 | McCabe et al. |
| 2010/0305644 A1 | 12/2010 | Spinelli et al. |
| 2011/0022110 A1 | 1/2011 | Min |
| 2011/0319954 A1 | 12/2011 | Niazi et al. |
| 2012/0041500 A1 | 2/2012 | Zhu et al. |
| 2012/0130442 A1 | 5/2012 | Rockweiler et al. |
| 2013/0030492 A1 | 1/2013 | Stadler et al. |
| 2013/0131749 A1 | 5/2013 | Sheldon et al. |

FOREIGN PATENT DOCUMENTS

| EP | 2 142 252 B1 | 8/2012 |
|---|---|---|
| WO | WO 2004/103470 A1 | 12/2004 |

OTHER PUBLICATIONS

Dendy et al., "Anodal Stimulation: An Underrecognized Cause of Nonresponders to Cardiac Resynchronization Therapy," *Indian Pacing and Electrophysiology Journal*, 2011; 11(3):64-72.
International Search Report and Written Opinion for International Application No. PCT/US2014/071514, mailed May 19, 2015; 11 pgs.

*Primary Examiner* — Amanda Patton
*Assistant Examiner* — Philip Edwards
(74) *Attorney, Agent, or Firm* — Carol F. Barry

(57) ABSTRACT

Systems and methods are described herein for determining whether anodal capture of the right ventricle is occurring when delivering left ventricular pacing with a cross-chamber pacing vector. The systems and methods may be measure cross-chamber sense times from left ventricular pacing and right ventricular pacing and compare the cross-chamber sense times to determine whether anodal capture of the right ventricle is occurring.

25 Claims, 7 Drawing Sheets

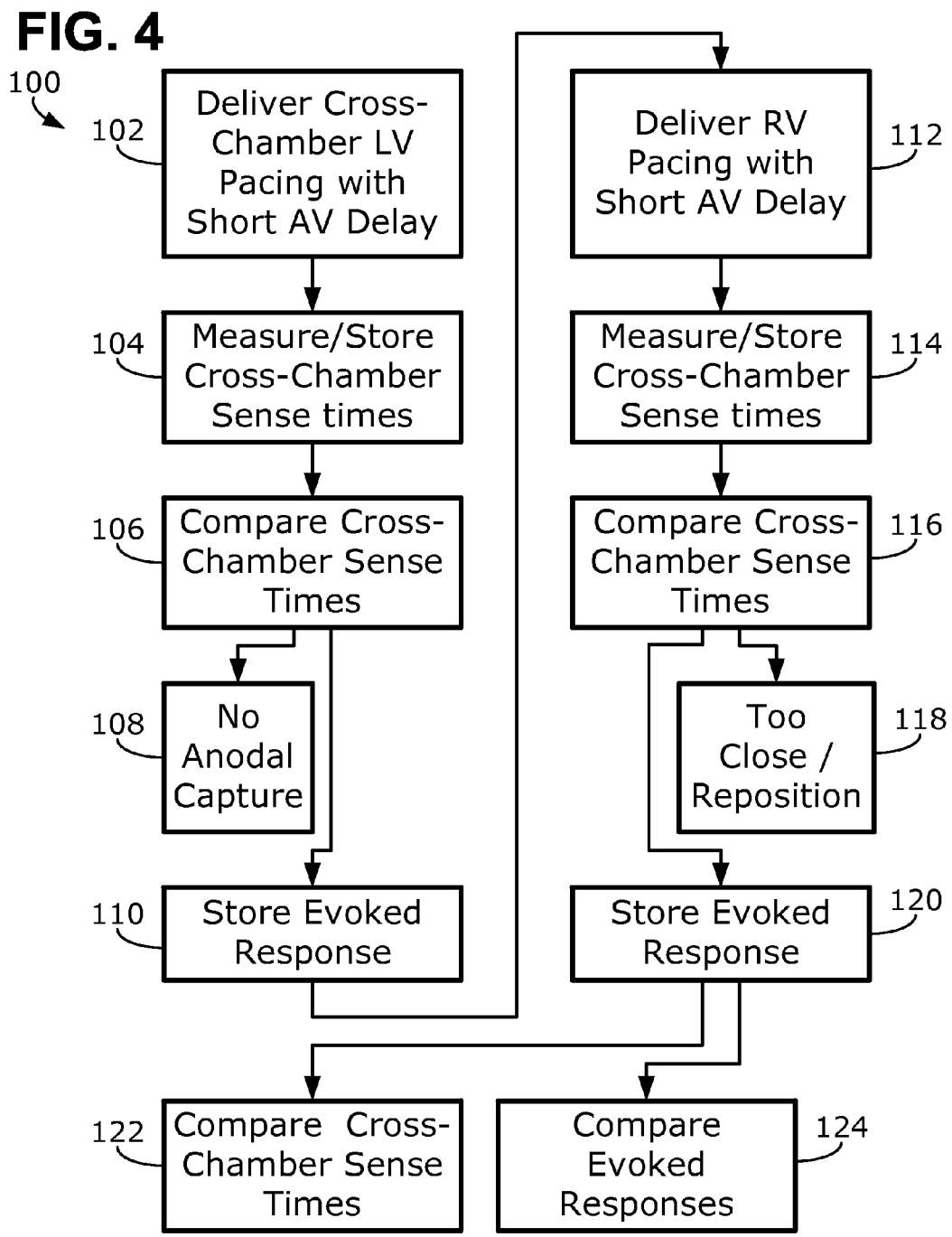

ANODAL CAPTURE DETECTION

The disclosure herein relates to systems and methods for use in the detection of anodal capture of the right ventricle during cardiac therapy. More specifically, the systems and methods may detect anodal capture of the right ventricle in pacing vectors having small cross-chamber electrode distances.

Cardiac resynchronization therapy (CRT) may be used to treat heart failure patients and may involve stimulation of the left ventricle or both right and left ventricles of a patient's heart using appropriately timed impulses. CRT devices may allow the option of a cross-chamber pacing vector for pacing the left ventricle (LV), e.g., from a LV tip electrode as the cathode, to the right ventricle, e.g., to a right ventricle (RV) coil electrode as the anode.

A pacing circuit may include two electrodes, a cathode and an anode, with the cathode proximate to the tissue or region of the heart which is intended to be stimulated. There may be a scenario when the tissue or region of the heart proximate to the anode is captured during pacing, resulting in anodal capture or stimulation. If anodal capture occurs when a LV pacing vector is used for cardiac resynchronization (e.g., a cross-chamber vector such as LV tip electrode to RV coil electrode, LV tip electrode to RV ring electrode, LV tip electrode to RV tip electrode, etc.), the right ventricle may be unintentionally captured instead of the left ventricle. Right ventricle capture may be especially undesirable in cases where the device is configured to deliver resynchronization therapy by pacing only the left ventricle. Also, in cases of biventricular pacing where interventricular timing delays are programmed within the device to optimize patient response, anodal stimulation may interfere with such optimization. Further, anodal capture, or stimulation, of the right ventricle in the setting of a cross-chamber LV pacing vector has been noted as a cause of non-response to CRT.

The ability to detect and provide warning of anodal capture, especially in the setting of a cross-chamber pacing vector configuration, may be an important device feature and may be helpful to both patients and physicians. Methods may compare morphologic features of evoked responses to LV only pacing with short bipole and extended bipolar configurations and may declare anodal capture if features of the evoked responses do not match. Such methods may not be specific to anodal capture because such methods may not account for cases when the distance between the RV and LV electrodes are small. For example, if the distance between the LV and RV electrodes is small, anodal capture (e.g., stimulation) from the RV electrode may result in similar evoked response morphology as pacing from a short LV bipolar configuration.

SUMMARY

The exemplary systems and methods described herein may be configured to determine whether anodal capture (e.g., undesired and/or unintended anodal stimulation) of the right ventricle is occurring in a cross-chamber pacing vector and to alert, or notify, a user (e.g., a physician) that anodal capture of the right ventricle is occurring. Additionally, the systems and methods may further determine and alert a user that the two electrodes in the cross-chamber pacing vector are too close or too proximate each other.

One exemplary implantable medical device for delivery of cardiac therapy to a patient may include electrode apparatus, a therapy delivery module configured to deliver pacing therapy using the electrode apparatus, a sensing module configured to sense electrical activity of the patient's heart using the electrode apparatus, and a control module coupled to the therapy delivery module and to the sensing module. The electrode apparatus may include at least one left ventricular electrode configured to be located proximate the left ventricle of a patient's heart and at least one right ventricular electrode configured to be located proximate the right ventricle of a patient's heart. The control module may be configured to deliver one or more left ventricular paces (e.g., a plurality of left ventricular paces) to the patient's left ventricle with a cross-chamber pacing vector using a selected left ventricular electrode of the at least one left ventricular electrode and a selected right ventricular electrode of the least one right ventricular electrode. The selected left ventricular electrode may be the cathode and the selected right ventricular electrode may be the anode in the cross-chamber pacing vector. The control module may be further configured to measure one or more first cross-chamber sense times (e.g., a plurality of first cross-chamber sense times) between the one or more left ventricular paces and one or more right ventricular senses in response to the one or more left ventricular paces, deliver one or more right ventricular paces (e.g., a plurality of right ventricular paces) to the patient's right ventricle using the selected right ventricular electrode, measure one or more second cross-chamber sense times (e.g., a plurality of second cross-chamber sense times) between the one or more right ventricular paces and one or more left ventricular senses in response to the one or more right ventricular paces, and determine whether anodal capture of the right ventricle is occurring when delivering ventricular pacing with the cross-chamber pacing vector based on the measured one or more first cross-chamber sense times and the measured one or more second cross-chamber sense times.

One exemplary method for use in providing cardiac therapy to a patient may include providing electrode apparatus (e.g., electrode apparatus may include at least one left ventricular electrode configured to be located proximate the left ventricle of a patient's heart and at least one right ventricular electrode configured to be located proximate the right ventricle of a patient's heart) and delivering one or more left ventricular paces (e.g., a plurality of left ventricular paces) with a cross-chamber pacing vector to the patient's left ventricle using a selected left ventricular electrode of the at least one left ventricular electrode and a selected right ventricular electrode of the least one right ventricular electrode. The selected left ventricular electrode may be the cathode and the selected right ventricular electrode may be the anode in the cross-chamber pacing vector. The exemplary method may further include measuring one or more first cross-chamber sense times (e.g., a plurality of first cross-chamber sense times) between the one or more left ventricular paces and one or more right ventricular senses in response to the one or more left ventricular paces, delivering one or more right ventricular paces (e.g., a plurality of right ventricular paces) to the patient's right ventricle using the selected right ventricular electrode, measuring one or more second cross-chamber sense times (e.g., a plurality of second cross-chamber sense times) between the one or more right ventricular paces and one or more left ventricular senses in response to the one or more right ventricular paces, and determining whether anodal capture of the right ventricle is occurring when delivering ventricular pacing with the cross-chamber pacing vector based on the measured one or more first cross-chamber sense times and the measured one or more second cross-chamber sense times.

In one or more embodiments, delivering one or more right ventricular paces to the patient's right ventricle using the selected right ventricular electrode may include delivering one or more right ventricular paces to the patient's right ventricle using the selected right ventricular electrode and another right ventricular electrode of the at least one right ventricular electrode in a short bipolar pacing vector. In one or more embodiments, delivering one or more left ventricular paces to the patient's left ventricle may include delivering one or more left ventricular paces to the patient's left ventricle using a selected short AV delay (e.g., to ensure capture), and delivering one or more right ventricular paces to the patient's right ventricle may include delivering one or more right ventricular paces to the patient's right ventricle using the selected short AV delay (e.g., to ensure capture, to prevent fusion with the patient's intrinsic AV conduction, etc.).

In one or more embodiments, at least one statistical metric may be computed for each of the one or more first cross-chamber sense times and the one or more second cross-chamber sense times. The at least one statistical metric may include at least one of a mean, median, and mode. Further, anodal capture of the right ventricle may be determined to be occurring when delivering ventricular pacing with the cross-chamber pacing vector by comparing the at least one statistical metric of the one or more first cross-chamber sense times to the at least one statistical metric of the one or more second cross-chamber sense times.

In one or more embodiments, determining whether anodal capture of the right ventricle is occurring when delivering ventricular pacing with the cross-chamber pacing vector may include determining that anodal capture of the right ventricle is occurring if the one or more second cross-chamber sense times are greater than or equal to the one or more first cross-chamber sense times plus a selected timed period. The selected time period may be greater than or equal to 20 milliseconds.

In one or more embodiments, at least one left ventricular paced evoked response in response to the one or more left ventricular paces and at least one right ventricular paced evoked response in response to the one or more right ventricular paces may be stored and anodal capture of the right ventricle may be determined to be occurring by comparing the at least one left ventricular paced evoked response and the at least one right ventricular paced evoked response. Further, the electrode apparatus may include at least one far-field electrode for monitoring far-field electrical activity configured to capture the at least one left ventricular evoked response and the at least one right ventricular evoked response.

In one or more embodiments, anodal capture of the right ventricle may be determined to not be occurring if the one or more first cross-chamber sense times are greater than a selected time interval (e.g., greater than or equal to about 60 milliseconds, etc.). In one or more embodiments, an alert may be provided if the one or more second cross-chamber sense times are less than or equal to a selected time interval (e.g., greater than or equal to about 60 milliseconds, etc.).

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIG. 4 is a flow diagram of an exemplary method for detection of anodal capture of the right ventricle.

DETAILED DESCRIPTION OF EXEMPLARY EMBODIMENTS

Figure 1:
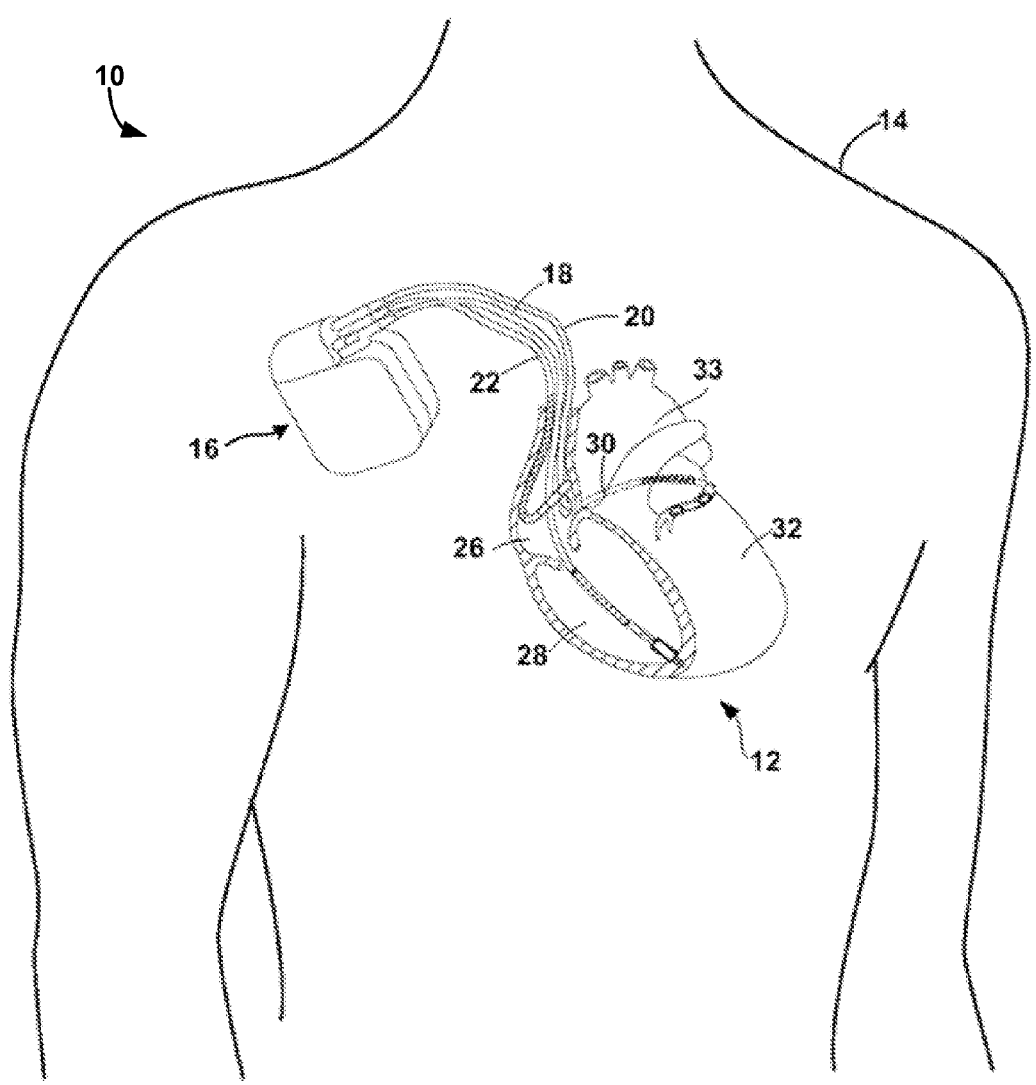
FIG. 1 is a diagram of an exemplary system including an exemplary implantable medical device (IMD).

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

The exemplary systems and methods may be configured to determine whether anodal capture (e.g., undesired and/or unintended anodal stimulation) of the right ventricle is occurring when delivering pacing therapy using a left ventricular cross-chamber pacing vector. The exemplary systems and methods may rule out, or exclude, cases of small inter-electrode distances between LV and RV electrodes when detecting anodal capture of the right ventricle. Also, the exemplary systems and methods may provide a warning of small inter-electrode distances (e.g., between the RV pacing electrode and the LV pacing electrode) during an implant procedure (e.g., a physical separation between the RV and LV electrodes may be desirable for CRT). The warning of small inter-electrode distances may alert the physician and provide the physician the option of repositioning either lead (e.g., RV lead or LV lead) for better separation and/or choosing a different LV electrode (e.g., if more than one LV electrode is available for pacing) to provide better separation (e.g., a larger inter-electrode distance). Better separation may also lead to more accurate detection of anodal capture (e.g., stimulation) of the right ventricle for cross-chamber pacing vectors.

In one or more embodiments, the exemplary systems and methods may provide a warning for small inter-electrode distances between the RV pacing electrode (i.e., the anode) and the LV pacing electrode (i.e., cathode) and further may distinguish between small inter-electrode distances and anodic capture of the right ventricle when a cross-chamber vector (e.g., an LV tip electrode to an RV coil electrode) is selected for LV pacing.

Exemplary systems and methods shall be described with reference to FIGS. 1-5. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary systems and methods described herein for use in determining anodal capture of the right ventricle when delivering may be used in conjunction with an exemplary therapy system 10 described herein with reference to FIGS. 1-3.

CRT systems and devices may deliver electrical pace pulses to the heart to produce contractions of the heart chambers in synchrony and at a rate sufficient to meet the patient's metabolic demand. Pacing therapy may involve the implementation of timing intervals between various events during a cardiac cycle. The timing intervals may be used to control the rate of heart chamber contractions and/or the synchrony between heart chamber contractions. For example, for patients whose intrinsic heart rate is too slow, pacing assists the heart in contracting at a rate that is sufficient to provide blood flow to meet the patient's metabolic requirements. For patients suffering from heart failure (HF), cardiac pacing may be used to ensure that the contractions of the heart chambers occur in a timed sequence that improves heart function.

FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. The IMD 16 may be configured to determine or identify effective electrodes located on the leads 18, 20, 22 using the exemplary methods and processes described herein. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., AV delay and other various timings, pulse wide, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. Exemplary cardiac resynchronization therapy systems and devices may include implantable electrodes configured in at least an extended bipolar configuration in which a left ventricular electrode defines a cathode of the extended bipolar configuration and a right ventricular electrode defines an anode of the extended bipolar configuration. To assist in determining anodal capture of the right ventricle for an extended bipolar configuration pacing vector (e.g., LV tip electrode to RV tip electrode) as described further herein, the implantable electrodes may be temporarily configured in at least a short bipolar configuration in which a first right ventricular electrode defines a cathode of the short bipolar configuration and a second right ventricular electrode (e.g., in close proximity to the first right ventricular electrode) defines an anode of the short bipolar configuration.

While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 2A:
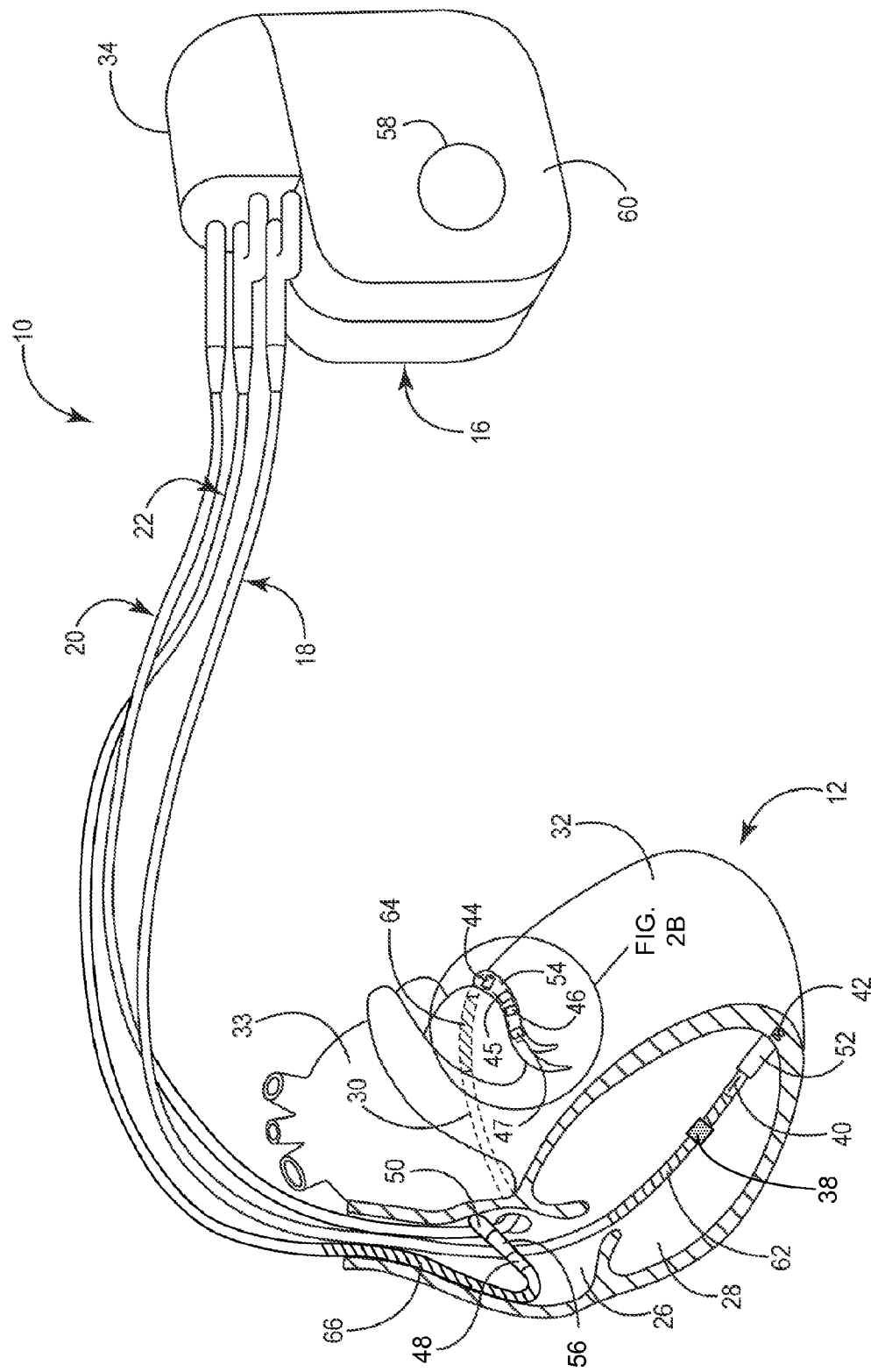
FIG. 2A is a diagram of the exemplary IMD of FIG. 1.
Figure 2B:
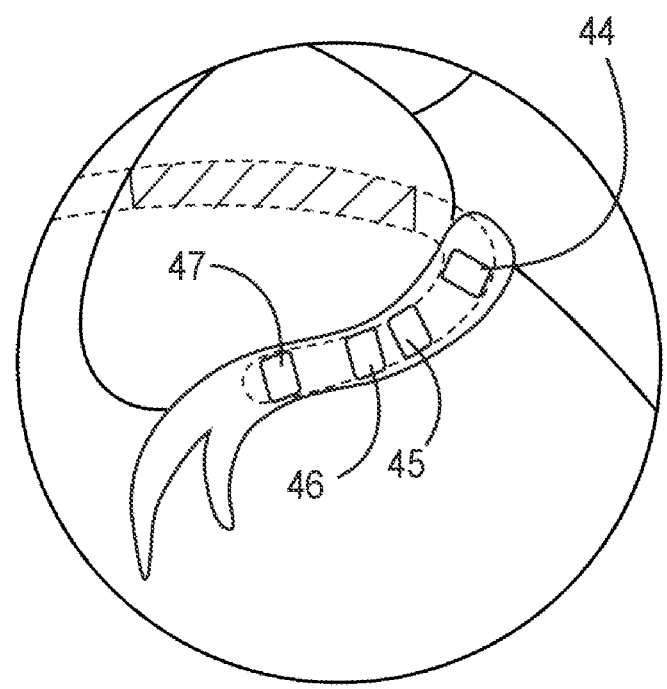
FIG. 2B is a diagram of an enlarged view of a distal end of the electrical lead disposed in the left ventricle of FIG. 2A.

FIGS. 2A-2B are conceptual diagrams illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 45, 46, 47 are located proximate to a distal end of the lead 20 and the bipolar electrodes 48, 50 are located proximate to a distal end of the lead 22.

The electrodes 40, 44, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The sensed electrical signals may be used to determine which of the electrodes 40, 42, 44, 45, 46, 47, 48, 50 are the most effective in improving cardiac function. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 2A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48 and 50 may be used for unipolar sensing or pacing in combination with housing electrode 58. In other words, any of electrodes 40, 42, 44, 45, 46, 47, 48, 50, 58 may be used in combination to form a sensing vector, e.g., a sensing vector that may be used to determine whether anodal capture of the right ventricle is occurring when delivering ventricular pacing therapy with a cross-chamber pacing vector, to evaluate and/or analyze the effectiveness of pacing therapy, etc. It is generally understood by those skilled in the art that other electrodes can also be selected to define, or be used for, pacing and sensing vectors. Further, any of electrodes 40, 42, 44, 45, 46, 47, 48, 50, 58, which are not being used to deliver pacing therapy, may be used to sense electrical activity during pacing therapy.

As described in further detail with reference to FIG. 2A, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity (e.g., for use in determining whether anodal capture of the right ventricle is occurring during pacing therapy, etc.) and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58 forming a RV elongated coil, or defibrillation electrode-to-housing electrode vector).

The configuration of the exemplary therapy system 10 illustrated in FIGS. 1-3 is merely one example. In other examples, the therapy system may include epicardial leads and/or patch electrodes instead of or in addition to the transvenous leads 18, 20, 22 illustrated in FIG. 1. Additionally, in other examples, the therapy system 10 may be implanted in/around the cardiac space without transvenous leads (e.g., leadless/wireless pacing systems) or with leads implanted (e.g., implanted transvenously) into the left chambers of the heart (in addition to or replacing the transvenous leads placed into the right chambers of the heart as illustrated in FIG. 1). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-3. Still further, other therapy systems may include a single lead that extends from the IMD 16 into the right atrium 26 or the right ventricle 28, or two leads that extend into a respective one of the right atrium 26 and the right ventricle 28.

Figure 3A:
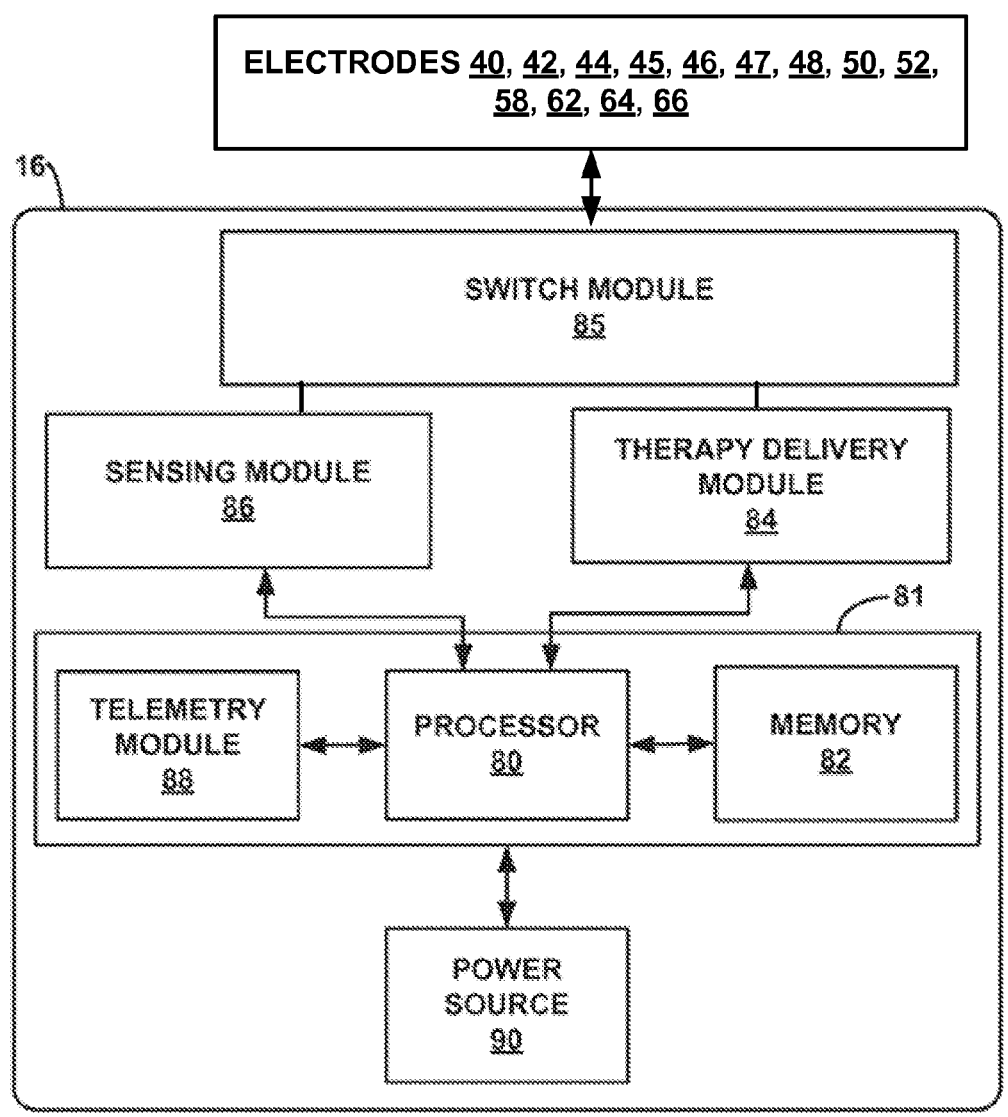
FIG. 3A is a block diagram of an exemplary IMD, e.g., the IMD of FIGS. 1-2.

FIG. 3A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may be used to determine the effectiveness of the electrodes 40, 42, 44, 45, 46, 47, 48, 50, 58, 62, 64, 66 using the exemplary methods and/or processes described herein according to a selected one or more programs, which may be stored in the memory 82. Further, the control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, pacing pulses with the amplitudes, pulse widths, frequency, or electrode polarities, etc., which may be specified by one or more selected therapy programs (e.g., AV delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, and 22, respectively, and/or helical tip electrodes 42 and 50 of leads 18 and 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may be also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 3B:
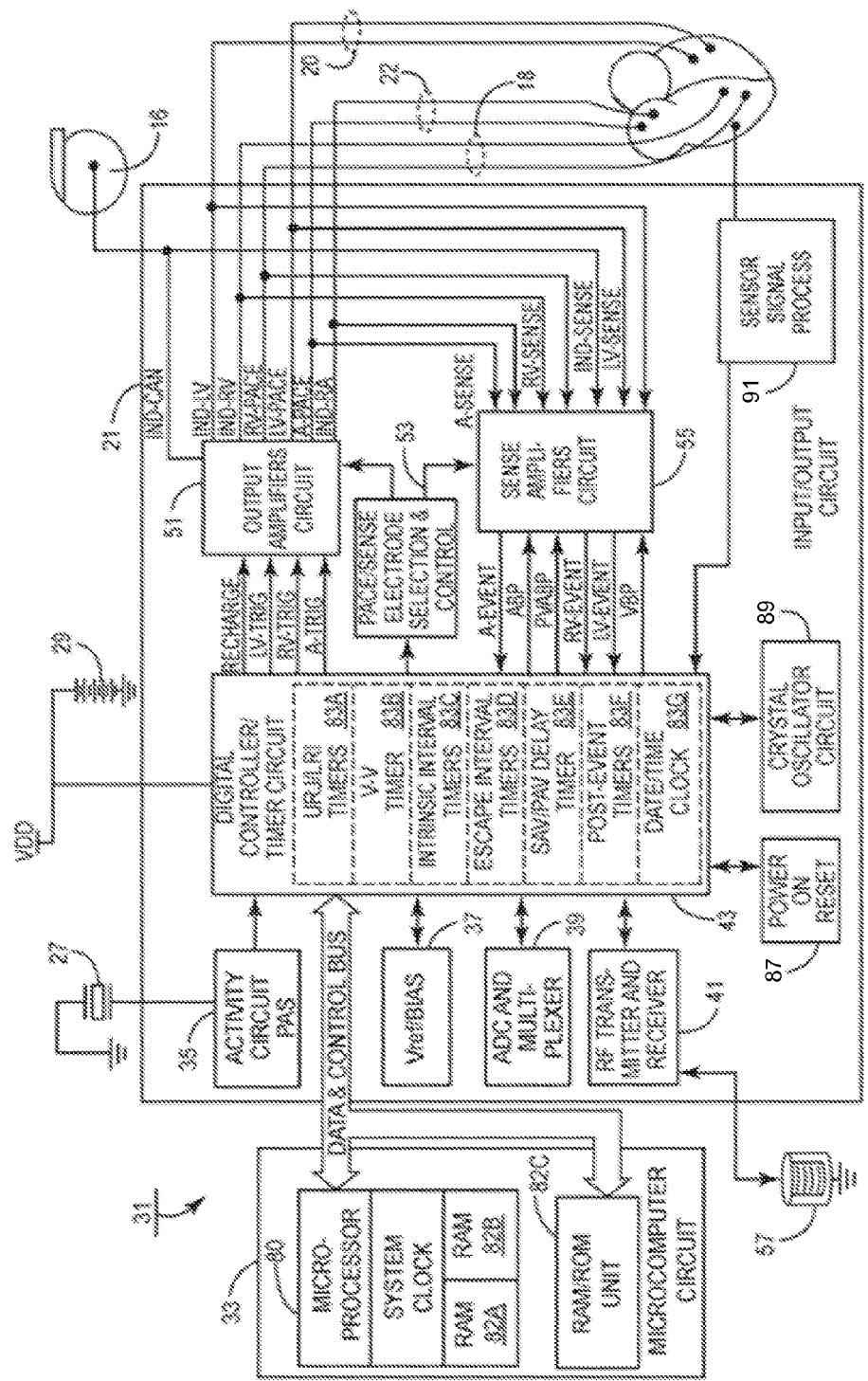
FIG. 3B is another block diagram of an exemplary IMD (e.g., an implantable pulse generator) circuitry and associated leads employed in the system and devices of FIGS. 1-2 for providing three sensing channels and corresponding pacing channels.

FIG. 3B is another embodiment of a functional block diagram for IMD 16. FIG. 3B depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 83 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21, while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21, while analog to digital converter ADC and multiplexer circuit 39 digitizes analog signals and voltage to provide real time telemetry if a cardiac signals from sense amplifiers 55, for uplink transmission via RF transmitter and receiver circuit 41. Voltage reference and bias circuit 37, ADC and multiplexer 39, power-on-reset circuit 87 and crystal oscillator circuit 89 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer as is well known in the art and its output signal is processed and used as the RCP. Sensor 27 generates electrical signals in response to sensed physical activity that are processed by activity circuit 35 and provided to digital controller/timer circuit 83. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which are incorporated herein by reference in their entireties. Similarly, the exemplary systems, apparatus, and methods described herein may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and marker channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 82 in a conventional manner. It is contemplated, however, that other implementations may be suitable to practice the exemplary systems and methods. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 320 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp delay as determined using known methods) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F time out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the $IND_{13}CAN$ electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

Anodal capture (e.g., stimulation) of the right ventricle may occur in cross-chamber pacing vectors such as, e.g., in extended bipolar configurations. For example, when using a pacing vector from a left ventricular electrode (as the cathode) to a right ventricular electrode (as the anode), undesirable anodal capture of the right ventricle may occur.

A flow diagram of an exemplary method for detection of anodal capture of the right ventricle when delivering ventricular pacing with a cross-chamber pacing vector is depicted in FIG. 4. The exemplary method 100 may use the systems, devices, methods, and apparatus as described herein with respect to FIGS. 1-3. For example, the exemplary method 100 may use electrode apparatus that includes one or more left ventricular electrodes configured to be located proximate the left ventricle of a patient's heart and one or more right ventricular electrodes configured to be located proximate the right ventricle of a patient's heart. The one or more left and right ventricular electrodes may be located on one or more leads, or may be wireless electrodes.

The exemplary method 100 may use the electrode apparatus to deliver one or more (e.g., one, a plurality, ten, etc.) cross-chamber left ventricular paces to the patient's left ventricle 102. To ensure capture of the left ventricle, a selected short AV delay may be used such as, e.g., less than or equal to about 10 milliseconds, less than or equal to about 20 milliseconds, less than or equal to about 30 milliseconds, less than or equal to about 60 milliseconds, etc. Further, in one or more embodiments, the one or more cross-chamber left ventricular paces may be delivered using one or more automatic capture control processes and techniques.

More specifically, the cross-chamber left ventricular paces may be configured to provide pacing to the patient's left ventricle using a selected left ventricular electrode of one or more left ventricular electrode and a selected right ventricular electrode of one or more right ventricular electrodes to form the cross-chamber pacing vector. In this configuration, the selected left ventricular electrode (e.g., LV tip electrode, LV ring electrode, etc.) is the cathode and the selected right ventricular electrode (e.g., RV tip electrode, RV ring electrode, RV coil electrode, etc.) is the anode in the cross-chamber pacing vector.

Figure 5:
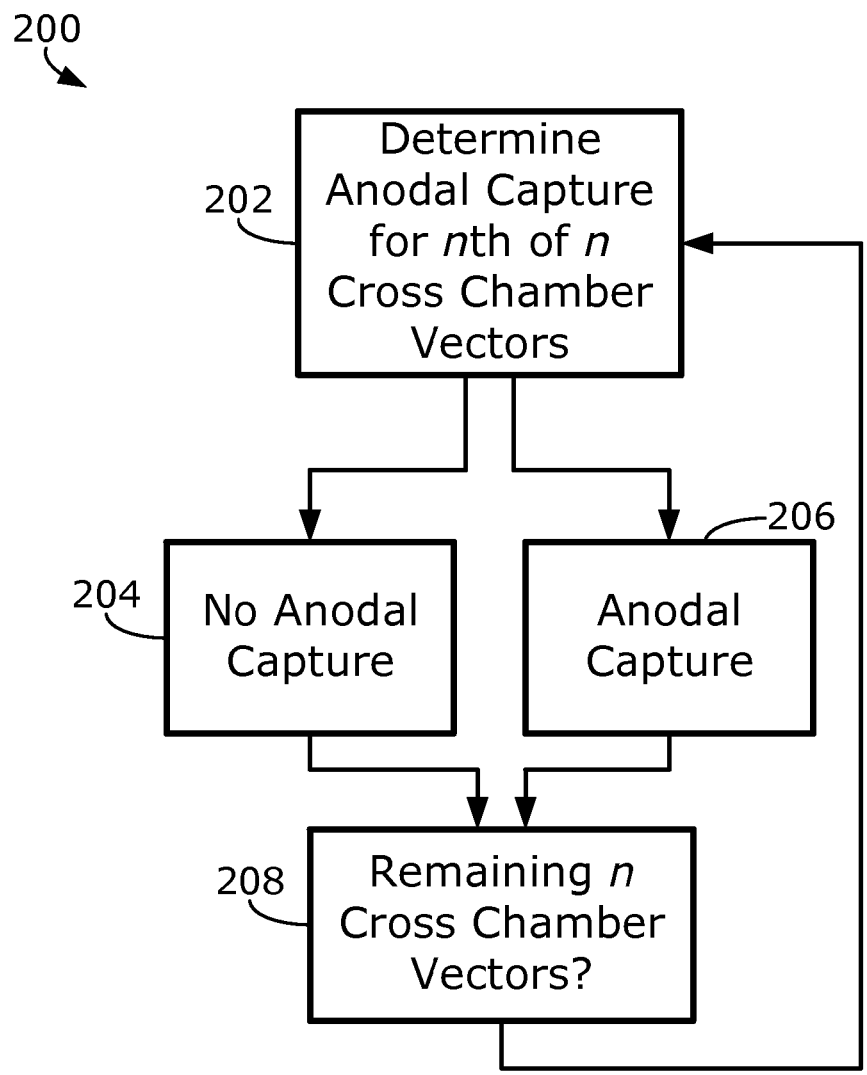
FIG. 5 is a flow diagram of an exemplary method for detection of anodal capture of the right ventricle using a plurality of cross-chamber pacing vectors.

Although a single cross-chamber pacing vector is used to deliver left ventricular pacing 102 in exemplary method 100, it is to be understood that more than one cross-chamber pacing vector may be evaluated, or tested, using method 100 as described herein with reference to the exemplary method of FIG. 5. Further, the selected cross-chamber pacing vector used to deliver left ventricular pacing 102 in exemplary method 100 may be the intended, or selected, pacing vector to deliver CRT to the patient (e.g., intended or selected by a physician). During implantation, immediately after implantation, and/or during follow-up examinations, the exemplary method 100 may be used to determine whether anodal capture (e.g., stimulation) of the right ventricle is undesirably occurring when using such cross-chamber pacing vector.

One or more (e.g., one, a plurality, five, etc.) first cross-chamber sense times between the one or more left ventricular paces and one or more right ventricular senses in response to the one or more left ventricular paces may be measured, or monitored, and stored 104 for use in evaluating whether anodal capture of the right ventricle is occurring when delivering ventricular pacing with a cross-chamber pacing vector. If a plurality of cross-chamber left ventricular paces are delivered to the patient's left ventricle 102, a plurality of first cross-chamber sense times may be measured, or monitored, and one or more statistical metrics may be computed based on the plurality of first cross-chamber sense times. For example, one or more of a mean, median, and mode may be generated (e.g., calculated, computed, determined, etc.) for the plurality of first cross-chamber sense times. The one or more statistical metrics (e.g., instead of each of the first cross-chamber sense times) may then be used to determine whether anodal capture of the right ventricle is occurring when delivering ventricular pacing with a cross-chamber pacing vector.

If the first cross-chamber sense times are short (e.g., less than about 60 milliseconds), anodal capture of the right ventricle may be suspected. Short first cross-chamber sense times, however, may be due to small inter-electrode distances. The exemplary method 100 may use the measured/stored one or more first cross-chamber sense times and/or statistical metrics based thereon to determine whether anodal capture of the right ventricle is not occurring (e.g., a lack of anodal stimulation) when delivering ventricular pacing therapy with the cross-chamber pacing vector if the first cross-chamber sense times are relatively long. In other words, relatively long first cross-chamber senses times may rule out undesirable anodal capture (e.g., stimulation) of the right ventricle. For example, the exemplary method 100 may compare the first cross-chamber sense times to a selected time interval 106. If the first cross-chamber sense times are greater than or equal to a selected time interval (e.g., about 20 milliseconds (ms), about 30 ms, about 40 ms, about 50 ms, about 60 ms, about 70 ms, about 80 ms, etc.), then the exemplary method 100 may determine that anodal capture of the right ventricle is not occurring using the selected cross-chamber pacing vector 108. In at least one embodiment, the exemplary method 100 may stop or end if it is determined that anodal capture of the right ventricle is not occurring with the cross-chamber pacing vector 108 (e.g., the cross-chamber pacing vector using the selected left ventricular electrode and the selected right ventricular electrode). The first cross-chamber sense times may be measured, or sensed, using a right ventricular sensing pair such as, e.g., RV tip electrode to RV ring electrode, RV tip electrode to RV coil electrode, etc. (e.g., short bipole configurations). The first cross-chamber sense times maybe defined between the left ventricular pace and the peak of the electrogram (e.g., a threshold, or peak, of the electrical signal may be at a level between about 0.3 millivolts to about 0.9 millivolts) sensed, e.g., using a short bipole configuration such as the RV tip electrode to RV ring electrode.

If the first cross-chamber sense times are less than the selected time interval, then the exemplary method 100 may continue to determine whether anodal capture of the right ventricular is occurring when delivering ventricular pacing with a cross-chamber pacing vector. For example, the method 100 may store one or more left ventricular evoked responses in response to the one or more left ventricular paces 110, which may be used in the exemplary method 100 to assist in determining whether anodal capture of the right ventricle is occurring. The left ventricular evoked responses may be any electrical response measured, or monitored, using any one or more electrodes. For example, the exemplary electrode apparatus may include one or more far-field electrodes for monitoring far-field electrical activity. The far-field electrodes may be configured to capture left ventricular evoked responses. The far-field electrodes may include, e.g., a device casing electrode (e.g., can electrode), a right ventricular coil electrode, etc.

The left ventricular evoked responses may be stored, or captured, in a template representative of and/or based on the plurality of left ventricular evoked responses in response to the one or more left ventricular paces over time. For example, a left ventricular template evoked response may be generated, or formed, based on a plurality of left ventricular evoked responses. The template may represent an average and/or any other statistical metric of the plurality of left ventricular evoked responses. In one or more embodiments, one or more left ventricular evoked responses may be determined to be outliers and may be removed from the plurality of left ventricular evoked responses when forming the template left ventricular evoked response. In one or more embodiments, a median left ventricular evoked response may be selected based on the plurality of left ventricular evoked responses to form the template left ventricular evoked response.

The exemplary method 100 may then deliver one or more (e.g., one, a plurality, ten, etc.) right ventricular paces to the patient's right ventricle using the selected right ventricular electrode 112. The selected right ventricular electrode may be the same right ventricular electrode used to form the cross-chamber pacing vector when delivery left ventricular pacing earlier 102 or a different electrode in the right ventricle (e.g., RV pacing may be performed using a RV tip electrode to RV ring electrode pacing vector to form a short bipolar pair, which may ensure that even if anodal capture/stimulation of the right ventricle occurs, it does not affect the left ventricle). To avoid effect of interference from the intrinsic conduction (e.g., fusion or pseudo-fusion), a selected short AV delay may be used such as, e.g., less than or equal to about 10 milliseconds, less than or equal to about 20 milliseconds, less than or equal to about 30 milliseconds, less than or equal to about 60 milliseconds, etc. Further, in one or more embodiments the one or more right ventricular paces may be delivered using automatic capture control processes and techniques. Additionally, a threshold amplitude (e.g., greater than or equal to about 0.5 millivolts) may be used for the right ventricular paces to ensure capture.

The right ventricular paces may be provided using another right ventricular electrode in conjunction with the selected right ventricular electrode in a short bipolar configuration. In this short bipolar configuration, the selected right ventricular electrode is the anode (e.g., remains the anode as in the cross-chamber pacing configuration from process 102) and the additional right ventricular electrode is the cathode. For example, the selected right ventricular electrode may be a RV tip electrode and the additional right ventricular electrode may be a RV ring electrode, RV coil electrode, etc.

One or more second cross-chamber sense times between the one or more right ventricular paces and one or more left ventricular senses in response to the one or more right ventricular paces may be measured, or monitored, and stored 114 for use in evaluating whether anodal capture of the right ventricle is occurring. If a plurality of right ventricular paces are delivered 112, a plurality of second cross-chamber sense times may be measured, or monitored, and one or more statistical metrics may be generated (e.g., computed, calculated, etc.) based on the plurality of second cross-chamber sense times. For example, one or more of a mean, median, and mode may be generated (e.g., calculated, computed, determined, etc.) for the plurality of second cross-chamber sense times. The one or more statistical metrics may then be used to determine whether anodal capture of the right ventricle is occurring when delivering ventricular pacing with the cross-chamber pacing vector (e.g., instead of each of the second cross-chamber sense times). The second cross-chamber sense times may be measured, or sensed, using a left ventricular sensing pair such as, e.g., LV tip electrode to LV ring electrode (e.g., a short bipole configuration). The second cross-chamber sense times maybe defined between the right ventricular pace and the peak of the electrogram sensed by the LV tip electrode to LV ring electrode. In absence of a LV ring electrode for a unipolar LV lead, the timing may be chosen off the timing of the steepest negative slope of a far-field LV cathode electrogram (e.g., LV tip electrode to device casing/can electrode, LV tip electrode to RV coil electrode, etc.).

The exemplary method 100 may use the measured/stored one or more first cross-chamber sense times and/or statistical metrics based thereon to determine whether the selected left ventricular electrode and the selected right ventricular electrode are too close and may need to be repositioned (e.g., during implantation, in follow-up examinations, etc.). For example, the exemplary method 100 may compare the second cross-chamber sense times to a selected time interval 116. If the second cross-chamber sense times are less than or equal to a selected time interval (e.g., about 20 milliseconds (ms), about 30 ms, about 40 ms, about 50 ms, about 60 ms, about 70 ms, about 80 ms, etc.), then the exemplary method 100 may determine that the selected left ventricular electrode and the selected right ventricular electrode are too close, or too proximate, to each other 118. An alert may be issued to a user to indicate to the user that the selected left ventricular electrode and the second right ventricular are too close or proximate to each other 118 such that, e.g., a user may re-position the right and left ventricular electrodes, a user may select different electrodes for the pacing vector, etc. In at least one embodiment, the alert may be delivered using telemetry to an external programmer. In at least another embodiment, the alert may be displayed on a graphical user interface of a computing device used to program and/or monitor the CRT system. The exemplary method 100 may stop or end if it is determined that the selected left and right electrodes are too close.

If the second cross-chamber sense times are greater than the selected time interval, then the exemplary method 100 may proceed to storing one or more right ventricular evoked responses in response to the one or more right ventricular paces 120, which may be used in the exemplary method 100 to assist in determining whether anodal capture of the right ventricle is occurring when delivering ventricular pacing with the cross-chamber pacing vector. Similar to the left ventricular evoked responses, the right ventricular evoked responses may be any electrical response measured, or monitored, using any one or more electrodes. The same one or more electrodes used to monitor/measure the left ventricular evoked responses may be used to monitor/measure the right ventricular evoked responses. For example, the exemplary electrode apparatus may include one or more far-field electrodes for monitoring far-field electrical activity. The far-field electrodes may be configured to capture the right ventricular evoked responses. The far-field electrodes may include, e.g., a device casing electrode (e.g., can electrode), right ventricular coil electrode, etc.

The right ventricular evoked responses may be stored, or captured, in a template representative of and/or based on the plurality of right ventricular evoked responses in response to the one or more left ventricular paces over time. For example, a right ventricular template evoked response may be generated, or formed, based on a plurality of right ventricular evoked responses. The template may represent an average and/or any other statistical metric of the plurality of right ventricular evoked responses. In one or more embodiments, one or more right ventricular evoked responses that are determined to be outliers may be removed from the plurality of right ventricular evoked responses to form the template right ventricular evoked response. In one or more embodiments, a median right ventricular evoked response may be selected based on the plurality of right ventricular evoked responses to be used in forming the template right ventricular evoked response.

The exemplary method 100 may perform one or processes to determine whether anodal capture of the right ventricle is occurring when delivering ventricular pacing with the cross-chamber pacing vector based on the data gathered and stored earlier such as, e.g., the first cross-chamber sense times, the second ventricular cross-chamber sense times, the left ventricular evoke responses, the right ventricular evoke responses, etc. For example, the exemplary method 100 may include determining that anodal capture of the right ventricle is occurring by comparing the first cross-chamber sense times (and/or statistical metrics based thereon) to the second cross-chamber sense times (and/or statistical metrics based thereon) 122. If the one or more second cross-chamber sense times (e.g., a median second cross-chamber sense time) are greater than or equal to the one or more first cross-chamber sense times (e.g., a median first cross-chamber sense time) plus a selected timed period, then it may be determined that anodal capture of the right ventricle is occurring during delivery of ventricular pacing with the cross-chamber pacing vector. If the one or more second cross-chamber sense times are less than the one or more first cross-chamber sense times plus the selected timed period, then it may be determined that anodal capture of the right ventricle is not occurring when delivering ventricular pacing with the cross-chamber pacing vector. The selected time period may be selected to ensure a significant amount of difference between a RV pace to LV sense and a LV pace to RV sense for detection of anodal capture of the right ventricle. In absence of anodal capture of the right ventricle, the cross-chamber sense times may be roughly equal but there may be some variations due to heterogeneous conduction, etc. The selected time period may be greater than or equal to about 10 milliseconds, greater than or equal to about 12 milliseconds, greater than or equal to about 15 milliseconds, greater than or equal to about 17 milliseconds, greater than or equal to about 20 milliseconds, greater than or equal to about 30 milliseconds, greater than or equal to about 40 milliseconds, greater than or equal to about 50 milliseconds, greater than or equal to about 60 milliseconds, greater than or equal to about 70 milliseconds, etc. The selected time period may be less than or equal to about 70 milliseconds, less than or equal to about 60 milliseconds, less than or equal to about 50 milliseconds, less than or equal to about 40 milliseconds, less than or equal to about 30 milliseconds, less than or equal to about 20 milliseconds, less than or equal to about 17 milliseconds, etc.

Further, for example, the exemplary method 100 may include determining whether undesirable anodal capture of the right ventricle is occurring when delivering ventricular pacing with the cross-chamber pacing vector by comparing the left ventricular evoked responses (and/or templates based thereon) and the right ventricular evoked responses (and/or templates based thereon) 124. In one or more embodiment, a percentage match may be calculated, or computed, between the left ventricular evoked responses and the right ventricular evoked responses, and if the percentage match is greater than or equal to 70%, then it may be determined that anodal capture of the right ventricle is occurring. Likewise, if the percentage match is less than 70%, then it may be determined that anodal capture of the right ventricle is not occurring. The exemplary systems and methods described herein may use percentage matching methods, processes, and systems described in U.S. Pat. No. 6,393,316 B1 issued on May 21, 2002 and entitled "Method and Apparatus for Detection and Treatment of Cardiac Arrhythmias," which is hereby incorporated by reference in its entirety.

The exemplary method 100 may be performed for more than one cross-chamber pacing vector. For example, more than one left ventricular electrode may be configured to pace the left ventricular as the cathode and more than one right ventricular electrode may be configured to be located in or proximate the right ventricle to be the anode. Each of these left and right ventricular electrodes may be used to form a plurality of cross-chamber pacing vectors, and the exemplary method 100 may be used to determine whether undesirable anodal capture of the right ventricle is occurring in each of the plurality of cross-chamber pacing vectors.

An exemplary method 200 for detection of anodal capture of the right ventricular when delivering ventricular pacing using a plurality of cross-chamber pacing vectors is depicted in FIG. 5. As shown, the exemplary method 200 may determine whether anodal capture of the right ventricle is occurring for an nth cross-chamber vector of n cross-chamber pacing vectors (e.g., a plurality of cross-chamber pacing vectors) using, e.g., the exemplary method 100 of FIG. 4. Anodal capture of the right ventricle for the n cross-chamber vector may be either determined to not be occurring 204 or be occurring 206. The exemplary method 200 may then continue if any remaining cross-chamber vectors are still available for determining whether anodal capture of the right ventricle is occurring 208.

The techniques, processes, and methods described in this disclosure, including those attributed to the IMD 16 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. An implantable medical device for delivery of cardiac therapy to a patient, the device comprising:
    electrode apparatus comprises at least one left ventricular electrode configured to be located proximate the left ventricle of a patient's heart and at least one right ventricular electrode configured to be located proximate the right ventricle of a patient's heart;
    a therapy delivery module configured to deliver pacing therapy using the electrode apparatus;
    a sensing module configured to sense electrical activity of the patient's heart using the electrode apparatus; and
    a control module coupled to the therapy delivery module and to the sensing module and configured to:
        deliver one or more left ventricular paces to the patient's left ventricle with a cross-chamber pacing vector using a selected left ventricular electrode of the at least one left ventricular electrode and a selected right ventricular electrode of the least one right ventricular electrode, wherein the selected left ventricular electrode is the cathode and the selected right ventricular electrode is the anode in the cross-chamber pacing vector;
        measure one or more first cross-chamber sense times between the one or more left ventricular paces and one or more right ventricular senses in response to the one or more left ventricular paces;
        deliver one or more right ventricular paces to the patient's right ventricle using the selected right ventricular electrode;
        measure one or more second cross-chamber sense times between the one or more right ventricular paces and one or more left ventricular senses in response to the one or more right ventricular paces; and
        determine whether anodal capture of the right ventricle is occurring when delivering ventricular pacing with the cross-chamber pacing vector based on the measured one or more first cross-chamber sense times and the measured one or more second cross-chamber sense times.

2. The device of claim 1, wherein delivering one or more right ventricular paces to the patient's right ventricle using the selected right ventricular electrode comprises delivering one or more right ventricular paces to the patient's right ventricle using the selected right ventricular electrode and another right ventricular electrode of the at least one right ventricular electrode in a short bipolar pacing vector.

3. The device of claim 1, wherein delivering one or more left ventricular paces to the patient's left ventricle comprises delivering one or more left ventricular paces to the patient's left ventricle using a selected short AV delay and delivering one or more right ventricular paces to the patient's right ventricle comprises delivering one or more right ventricular paces to the patient's right ventricle using the selected short AV delay.

4. The device of claim 1, wherein the one or more left ventricular paces comprises a plurality of left ventricular paces, wherein the one or more first cross-chamber sense times comprise a plurality of first cross-chamber sense times, wherein the one or more right ventricular paces comprises a plurality of right ventricular paces, wherein the one or more second cross-chamber sense times comprise a plurality of second cross-chamber sense times.

5. The device of claim 1, wherein the control module is further configured to:
compute at least one statistical metric for the one or more first cross-chamber sense times and the one or more second cross-chamber sense times, wherein the at least one statistical metric comprises at least one of a mean, median, and mode; and
determine whether anodal capture of the right ventricle is occurring when delivering ventricular pacing with the cross-chamber pacing vector by comparing the at least one statistical metric of the one or more first cross-chamber sense times to the at least one statistical metric of the one or more second cross-chamber sense times.

6. The device of claim 1, wherein determining whether anodal capture of the right ventricle is occurring when delivering ventricular pacing with the cross-chamber pacing vector comprises determining that anodal capture of the right ventricle is occurring if the one or more second cross-chamber sense times are greater than or equal to the one or more first cross-chamber sense times plus a selected timed period, wherein the selected time period is greater than or equal to 20 milliseconds.

7. The device of claim 1, wherein the control module is further configured to:
store at least one left ventricular paced evoked response in response to the one or more left ventricular paces;
store at least one right ventricular paced evoked response in response to the one or more right ventricular paces; and
determine whether anodal capture of the right ventricle is occurring when delivering ventricular pacing with the cross-chamber pacing vector by comparing the at least one left ventricular paced evoked response and the at least one right ventricular paced evoked response.

8. The device of claim 7, wherein the electrode apparatus comprises at least one far-field electrode for monitoring far-field electrical activity configured to capture the at least one left ventricular evoked response and the at least one right ventricular evoked response.

9. The device of claim 1, wherein the control module is further configured to determine that anodal capture of the right ventricle is not occurring if the one or more first cross-chamber sense times are greater than or equal to a selected time interval.

10. The device of claim 9, wherein the selected time interval value is greater than or equal to about 60 milliseconds.

11. The device of claim 1, wherein the control module is further configured to provide an alert if the one or more second cross-chamber sense times are less than a selected time interval.

12. The device of claim 11, wherein the selected time interval is greater than or equal to about 60 milliseconds.

13. A method for use in providing cardiac therapy to a patient comprising:
providing electrode apparatus comprising at least one left ventricular electrode configured to be located proximate the left ventricle of a patient's heart and at least one right ventricular electrode configured to be located proximate the right ventricle of a patient's heart;
delivering one or more left ventricular paces to the patient's left ventricle with a cross-chamber pacing vector using a selected left ventricular electrode of the at least one left ventricular electrode and a selected right ventricular electrode of the least one right ventricular electrode, wherein the selected left ventricular electrode is the cathode and the selected right ventricular electrode is the anode in the cross-chamber pacing vector;
measuring one or more first cross-chamber sense times between the one or more left ventricular paces and one or more right ventricular senses in response to the one or more left ventricular paces;
delivering one or more right ventricular paces to the patient's right ventricle using the selected right ventricular electrode;
measuring one or more second cross-chamber sense times between the one or more right ventricular paces and one or more left ventricular senses in response to the one or more right ventricular paces; and
determining whether anodal capture of the right ventricle is occurring when delivering ventricular pacing with the cross-chamber pacing vector based on the measured one or more first cross-chamber sense times and the measured one or more second cross-chamber sense times.

14. The method of claim 13, wherein delivering one or more right ventricular paces to the patient's right ventricle using the selected right ventricular electrode comprises delivering one or more right ventricular paces to the patient's right ventricle using the selected right ventricular electrode and another right ventricular electrode of the at least one right ventricular electrode in a short bipolar pacing vector.

15. The method of claim 13, wherein delivering one or more left ventricular paces to the patient's left ventricle comprises delivering one or more left ventricular paces to the patient's left ventricle using a selected short AV delay and delivering one or more right ventricular paces to the patient's right ventricle comprises delivering one or more right ventricular paces to the patient's right ventricle using the selected short AV delay.

16. The method of claim 13, wherein the one or more left ventricular paces comprises a plurality of left ventricular paces, wherein the one or more first cross-chamber sense times comprise a plurality of first cross-chamber sense times, wherein the one or more right ventricular paces comprises a plurality of right ventricular paces, wherein the one or more second cross-chamber sense times comprise a plurality of second cross-chamber sense times.

17. The method of claim 13, wherein the method further comprises:

computing at least one statistical metric for the one or more first cross-chamber sense times and the one or more second cross-chamber sense times, wherein the at least one statistical metric comprises at least one of a mean, median, and mode; and determining whether anodal capture of the right ventricle is occurring when delivering ventricular pacing with the cross-chamber pacing vector by comparing the at least one statistical metric of the one or more first cross-chamber sense times to the at least one statistical metric of the one or more second cross-chamber sense times.

18. The method of claim 13, wherein determining whether anodal capture of the right ventricle is occurring when delivering ventricular pacing with the cross-chamber pacing vector comprises determining that anodal capture of the right ventricle is occurring if the one or more second cross-chamber sense times are greater than or equal to the one or more first cross-chamber sense times plus a selected timed period, wherein the selected time period is greater than or equal to 20 milliseconds.

19. The method of claim 13, wherein method further comprises:
storing at least one left ventricular paced evoked response in response to the one or more left ventricular paces;
storing at least one right ventricular paced evoked response in response to the one or more right ventricular paces; and
determining whether anodal capture of the right ventricle is occurring when delivering ventricular pacing with the cross-chamber pacing vector by comparing the at least one left ventricular paced evoked response and the at least one right ventricular paced evoked response.

20. The method of claim 19, wherein the electrode apparatus comprises at least one far-field electrode for monitoring far-field electrical activity configured to capture the at least one left ventricular evoked response and the at least one right ventricular evoked response.

21. The method of claim 13, wherein the method further comprise determining that anodal capture of the right ventricle is not occurring if the one or more first cross-chamber sense times are greater than or equal to a selected time interval.

22. The method of claim 21, wherein the selected time interval value is greater than or equal to about 60 milliseconds.

23. The method of claim 13, wherein the method further comprises providing an alert if the one or more second cross-chamber sense times are less than a selected time interval.

24. The method of claim 23, wherein the selected time interval is greater than or equal to about 60 milliseconds.

25. An implantable medical device for delivery of cardiac therapy to a patient, the device comprising:
electrode apparatus comprises at least one left ventricular electrode configured to be located proximate the left ventricle of a patient's heart and at least one right ventricular electrode configured to be located proximate the right ventricle of a patient's heart;
a therapy delivery module configured to deliver ventricular pacing to at least the patient's left ventricle using a cross-chamber pacing vector using a selected left ventricular electrode of the at least one left ventricular electrode and a selected right ventricular electrode of the least one right ventricular electrode, wherein the selected left ventricular electrode is the cathode and the selected right ventricular electrode is the anode in the cross-chamber pacing vector;
a sensing module configured to sense electrical activity of the patient's heart using the electrode apparatus; and
a control module coupled to the therapy delivery module and to the sensing module and configured to determine whether anodal capture of the right ventricle is occurring when delivering ventricular pacing with the cross-chamber pacing vector based on at least:
one or more cross-chamber sense times between one or more left ventricular paces and one or more right ventricular senses in response to the one or more left ventricular paces, and
one or more second cross-chamber sense times between one or more right ventricular paces and one or more left ventricular senses in response to the one or more right ventricular paces.

* * * * *